United States Patent
Bouali et al.

(10) Patent No.: US 11,607,119 B2
(45) Date of Patent: Mar. 21, 2023

(54) FLUORESCENCE LIFETIME SPECTROSCOPY BASED CAPSULE ENDOSCOPY

(71) Applicant: QATAR UNIVERSITY, Doha (QA)

(72) Inventors: Moez Bouali, Montreal (CA);
Mohamad Sawan, Montreal (CA);
Sumaya Al-Maadeed, Doha (QA);
Ahmed Bouridane, Newcastle upon Tyne (GB)

(73) Assignee: QATAR UNIVERSITY, Doha (QA)

( * ) Notice: Subject to any disclaimer, the term of this patent is extended or adjusted under 35 U.S.C. 154(b) by 537 days.

(21) Appl. No.: 16/222,915

(22) Filed: Dec. 17, 2018

(65) Prior Publication Data
US 2020/0187762 A1    Jun. 18, 2020

(51) Int. Cl.
| A61B 1/04 | (2006.01) |
| A61B 5/07 | (2006.01) |
| A61B 5/00 | (2006.01) |

(52) U.S. Cl.
CPC ............ *A61B 1/041* (2013.01); *A61B 5/0071* (2013.01); *A61B 5/0075* (2013.01); *A61B 5/073* (2013.01); *A61B 5/4255* (2013.01); *A61B 5/6861* (2013.01); *A61B 5/0031* (2013.01)

(58) Field of Classification Search
CPC ............ A61B 1/00006; A61B 1/00016; A61B 1/00032; A61B 1/041; A61B 1/063; A61B 5/0071; A61B 5/0084; A61B 5/073
See application file for complete search history.

(56) References Cited

U.S. PATENT DOCUMENTS

| 9,572,273 | B2 * | 2/2017 | Blunier ............... A61B 5/14503 |
| 2003/0165428 | A1 * | 9/2003 | McCombs .......... A61K 49/0034 424/9.2 |
| 2004/0054278 | A1 | 3/2004 | Kimchy et al. |
| 2005/0029437 | A1 * | 2/2005 | Hasegawa .......... G02B 23/2407 250/226 |
| 2005/0130167 | A1 * | 6/2005 | Bao ....................... G01N 33/587 435/6.12 |

(Continued)

OTHER PUBLICATIONS

Demosthenous, P., et al. "Infrared fluorescene-based cancer screening capsule for the small intestine" *IEEE Transactions on Biomedical Circuits and Systems* Apr. 2016, vol. 10, No. 2, pp. 467-476.

(Continued)

*Primary Examiner* — Baisakhi Roy
(74) *Attorney, Agent, or Firm* — Squire Patton Boggs (US) LLP (57) ABSTRACT

An ingestible capsule for detecting cancerous and non-cancerous tissues in a colon of patient is disclosed. The capsule has a radiation source integrated into the capsule body for illuminating tissues within a colon of the patient. Tissues of the colon are irradiated with radiation from the radiation source to elicit a fluorescence response, and a photon detector measures photons of the fluorescence response. Intensity and fluorescence lifetime of the fluorescence response is determined based on measured photons. A system employing the capsule is configured to distinguish cancerous and non-cancerous tissues based on the determined fluorescence lifetime of the fluorescence response.

8 Claims, 5 Drawing Sheets

(56) References Cited

U.S. PATENT DOCUMENTS

| | | | |
|---|---|---|---|
| 2005/0154277 A1* | 7/2005 | Tang | A61B 1/00156 600/407 |
| 2005/0215911 A1* | 9/2005 | Alfano | A61B 5/0071 600/476 |
| 2007/0238921 A1* | 10/2007 | Weirich | A61B 1/041 600/109 |
| 2008/0262312 A1* | 10/2008 | Carroll | A61B 1/07 600/160 |
| 2009/0030279 A1* | 1/2009 | Zander | A61B 5/073 600/118 |
| 2009/0135245 A1* | 5/2009 | Luo | H04N 5/3745 348/222.1 |
| 2009/0216079 A1* | 8/2009 | Morgan | A61B 1/041 600/109 |
| 2010/0198061 A9 | 8/2010 | Daghlghian et al. | |
| 2012/0022338 A1* | 1/2012 | Subramaniam | A61B 5/0095 600/407 |
| 2012/0116162 A1* | 5/2012 | Kawano | A61B 34/73 600/118 |
| 2012/0150045 A1 | 6/2012 | Matsumoto et al. | |
| 2013/0331647 A1 | 12/2013 | Gingras | |
| 2015/0148626 A1* | 5/2015 | Sella-Tavor | C12Q 1/6886 600/314 |
| 2016/0377543 A1 | 12/2016 | Rothberg et al. | |
| 2018/0164221 A1* | 6/2018 | Singh | A61B 5/4255 |
| 2018/0279908 A1* | 10/2018 | Jones | A61B 5/6861 |
| 2019/0015038 A1* | 1/2019 | Finkelstein | A61B 5/0071 |
| 2019/0069815 A1* | 3/2019 | Burnes | A61B 5/0031 |
| 2019/0374207 A1* | 12/2019 | Jones | A61B 5/0086 |
| 2020/0114171 A1* | 4/2020 | Tortora | A61N 5/0624 |
| 2020/0196873 A1* | 6/2020 | Ntziachristos | A61B 1/00147 |
| 2021/0109340 A1* | 4/2021 | Liang | A61B 1/00177 |

OTHER PUBLICATIONS

Al-Rawhani, Mohammed A., et al. "Design and implementation of a wireless capsule suitable for autofluorescence intensity detection in biological tissues." *IEEE Transactions on Biomedical Engineering* Jan. 1, 2013, vol. 60, No. 1, pp. 55-62.

International Search Report and Written Opinion dated Apr. 27, 2020 for International Application No. PCT/IB19/60874; 14 pages.

\* cited by examiner

FLUORESCENCE LIFETIME SPECTROSCOPY BASED CAPSULE ENDOSCOPY

BACKGROUND OF THE INVENTION

Field of the Invention

This invention concerns a device and method for early detection of colorectal disease, in particular, an ingestible capsule utilizing fluorescence lifetime spectroscopy to screen for and detect cancerous tissue in a patient.

Description of the State of the Art

The early detection and diagnosis of colorectal cancer continues to be high importance. For example, in the Gulf Cooperation Council (GCC) states (Qatar, Kuwait, Oman, Saudi Arabia, Bahrain, and United Arab Emirates (UAE)), colorectal cancer was ranked the first most common type of cancer in the male population at 9.2% and the third most diagnosed cancer in the female population at 7.6% for a period of 12 years (1998-2009).

If diagnosed at an earlier stage, two-thirds of colorectal cancers could be prevented or cured. White light colonoscopy is currently considered to be the gold standard for colon evaluation and screening. Although it has high sensitivity and selectivity, many persons are reluctant to undergo colonoscopy because of its discomfort. A portable and comfortable alternative to colonoscopy has become urgent. An emerging technology using capsule endoscopy could be an alternative to white light colonoscopy. First introduced in 2011 for small intestine exploring, the capsule endoscopy rapidly became the best alternative to white light colonoscopy.

Since 2014, Medtronic has commercialized a capsule for colon investigation called PillCam colon 2. PillCam colon is the only existing commercialized capsule endoscopy for the large intestine. The existing capsule uses white light illumination and a color camera to image and record the interior of the colon. Specifically, it uses a white light CCD camera combined with six LEDs to generate color images of the colon and rectum mucosa.

A disadvantage of the PillCam is that white light imaging has been proven not to have a good sensitivity for earlier or non-polypoid neoplasia. Therefore, the white light capsule endoscopy PillCam colon by Medtronic for colon exploration suffers from the low sensitivity of this white light in detecting early and non-polypoid colorectal neoplasia.

Fluorescence spectroscopy has been shown to enhance the sensitivity and specificity of detection of neoplasia. A fluorescence intensity measurements endoscope has been commercialized by Olympus Corporation. The autofluorescence measurement permits improvement of the sensitivity and selectivity of lesions detection compared to traditional white light colonoscope especially for small polyps <5 mm in diameter. However, this endoscope suffers from a bulky design, high cost and high-power consumption, and it can only measure the intensity of endogenous fluorophore.

Al-Rawhani et al. ("Design and Implementation of a Wireless Capsule Suitable for Autofluorescence Intensity Detection in Biological Tissues," IEEE Transactions on Biomedical Engineering, 60(1), 55-62, October 2012) disclose autofluorescence capsule endoscopy for small intestine lesion detection. The capsule is capable of detecting the emission intensity of gastrointestinal endogenous fluorophores at 520 nm. The capsule is composed of two blue LEDs sources for illumination purpose and two commercialized multi-pixel photon counters (MPPCs) for detection purposes. This capsule suffers from lack of sensitivity due to background noise from other endogenous fluorophores. Since LEDs have a relatively large spectral bandwidth of 20 nm to 40 nm, other fluorophores sensitive to blue light will be excited, and thus emit light at the same time around 520 nm. Since MPPCs are sensitive to light from 350 nm to 900 nm, the read signal will match not only to a specific fluorophore, but to many of them. Thus, the detection results will be incorrect.

A possible solution to this background noise is the use of exogenous fluorophores beyond the visible region, since all endogenous fluorophores in the gastrointestinal tract emit in this visible spectrum. Demosthenous et al. ("Infrared Fluorescence-Based Cancer Screening Capsule for the Small Intestine," IEEE transactions on biomedical circuits and systems, 10(2), 467-476, April 2016) introduced a fluorescence based capsule endoscopy capable of measuring the intensity of indocyanine green (ICG), which is a Near Infrared (NIR) fluorophore, in the gastrointestinal tract. The fluorophore is excited in the NIR region at 780 nm by six laser diodes, and the intensity measurement is done by six standard photodiodes at 850 nm. Since the emitted ICG signal is so low, in the order of nanowatts, it is impossible to measure this weak intensity by using standard photodiodes with no internal gain.

As a solution, Demosthenous et al. proposed to amplify the ICG detected signals using six amplifiers. The use of amplifiers increases the readout noise due to the amplification process and thus reduces the input dynamic range and the signal to noise ratio. However, measuring fluorescence intensity differences between normal and abnormal tissues to characterize the health stature of the gastrointestinal tract is problematic since the measured intensity depends on many environmental parameters (source, detector, sensitivity peak, background, etc.).

Therefore, what is needed is a capsule for colon investigation without the shortcomings of currently commercialized devices and solutions proposed in the prior art literature.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if each said individual publication, patent, or patent application was fully set forth, including any figures, herein.

SUMMARY OF THE INVENTION

Briefly and in general terms, the present invention is directed to a capsule, system, and method for investigating tissue and/or detecting cancerous and non-cancerous tissues.

An aspects of the invention, a capsule comprises a capsule body, an excitation module, and a detection module. The excitation module comprises at least one light source configured to generate near-infrared light that elicits a fluorescence response from tissue of a patient. The detection module comprising at least one photodetector configured to detect photons resulting from the fluorescence response.

An aspects of the invention, a system comprises the capsule and a device. The capsule comprises a communication module in the capsule body. The communication module comprises electronic components configured to transmit decay data using radio signals while the capsule is in the patient, the decay data representative of decay of intensity of the fluorescence response. The device is configured to receive the decay data from the capsule while the capsule is in the patient and while the device is external to the patient. The device is configured to use the received decay data to calculate a fluorescence lifetime of the fluorescence response.

An aspects of the invention, a method comprises: administering a capsule to a patient; when the capsule is in the patient, emitting near-infrared light from at least one light source in the capsule to elicit a fluorescence response from a tissue within the patient; and detecting, by at least one photodetector in the capsule, photons resulting from the fluorescence response.

The features and advantages of the invention will be more readily understood from the following detailed description which should be read in conjunction with the accompanying drawings.

DETAILED DESCRIPTION OF THE INVENTION

As used herein, "fluorescence" refers to exciting a substance with light or radiation in which the light hitting a sample puts atoms, ions or molecules (fluorophores) in the sample into excited states from where they decay into lower-lying states (e.g. their ground states) through spontaneous emission of fluorescence photons.

The "fluorescence lifetime" or FLT is a measure of the time a fluorophore spends in the excited state before returning to the ground state by emitting a photon. The lifetimes of fluorophores can range from picoseconds to hundreds of nanoseconds.

Fluorescence-lifetime imaging microscopy or FLIM is an imaging technique for producing an image based on the differences in the exponential decay rate of the fluorescence from a fluorescent sample. It can be used as an imaging technique in confocal microscopy, two-photon excitation microscopy, and multiphoton tomography.

As used herein, the near-infrared range is from 700 nm to 2500 nm. Near-infrared light is electromagnetic radiation having wavelengths within the near-infrared range.

This invention concerns a method for early detection of colorectal cancerous tissue. The method is based on fluorescence lifetime spectroscopy. An ingestible capsule-based device is projected to screen for and detect cancerous tissue in a patient. If a colorectal disease is diagnosed at an early stage, two-thirds of colorectal cancers could be prevented or cured. White light colonoscopy is currently considered to be the gold standard for colon evaluation and screening. Although it has high sensitivity and selectivity, patients are reluctant to undergo colonoscopy because of its discomfort. A portable and comfortable alternative to colonoscopy has become urgent. An emerging technology using capsule endoscopy could be an alternative to white light colonoscopy. Such capsule endoscopy is the subject of this patent.

Most colorectal cancer or colorectal neoplasia begins as a growth called a polyp on the inner lining of the colon or rectum. Some types of polyps can change into cancer over the course of several years, but not all polyps become cancer. The morphology of colonic lesions depends on the direction of proliferation growth. Two main macroscopic types may be recognized as superficial lesions and advanced cancers. Lesions with superficial appearance can be classified as polypoid type, non-polypoid types, and mixed types. In the Paris classification system, polypoid type are defined as elevated more than 2.5 mm above the mucosal layer and non-polypoid types are slightly elevated less than 2.5 mm, flat or slightly depressed. The threshold of 2.5 mm, corresponds to the height of a closed biopsy forceps. Non-polypoid lesions are usually flat or slightly elevated and tend to spread laterally. Non-polypoid types that are flat or depressed may be found throughout the colon unlike polypoid cancers are more frequent in the left part.

The chance of changing into a cancer depends on the kind of polyp. Two main types of polyps are adenomatous polyps (adenomas) in one hand, and hyperplastic polyps and inflammatory polyps in the other hand. Adenomatous polyps sometimes change into cancer. Because of this, adenomas are called a pre-cancerous condition. Hyperplastic polyps and inflammatory polyps are more common, but in general they are not pre-cancerous. Other polyp characteristics that can increase the chances a polyp may contain cancer or increase someone's risk of developing colorectal cancer besides the type include the size (larger than 1 cm), the number found (more than two), and if dysplasia is seen in the polyp after it is removed. Dysplasia, another pre-cancerous condition, is an area in a polyp or in the lining of the colon or rectum where the cells look abnormal (but not like true cancer cells). If cancer forms in a polyp, it can eventually begin to grow into the wall of the colon or rectum.

Figure 1:
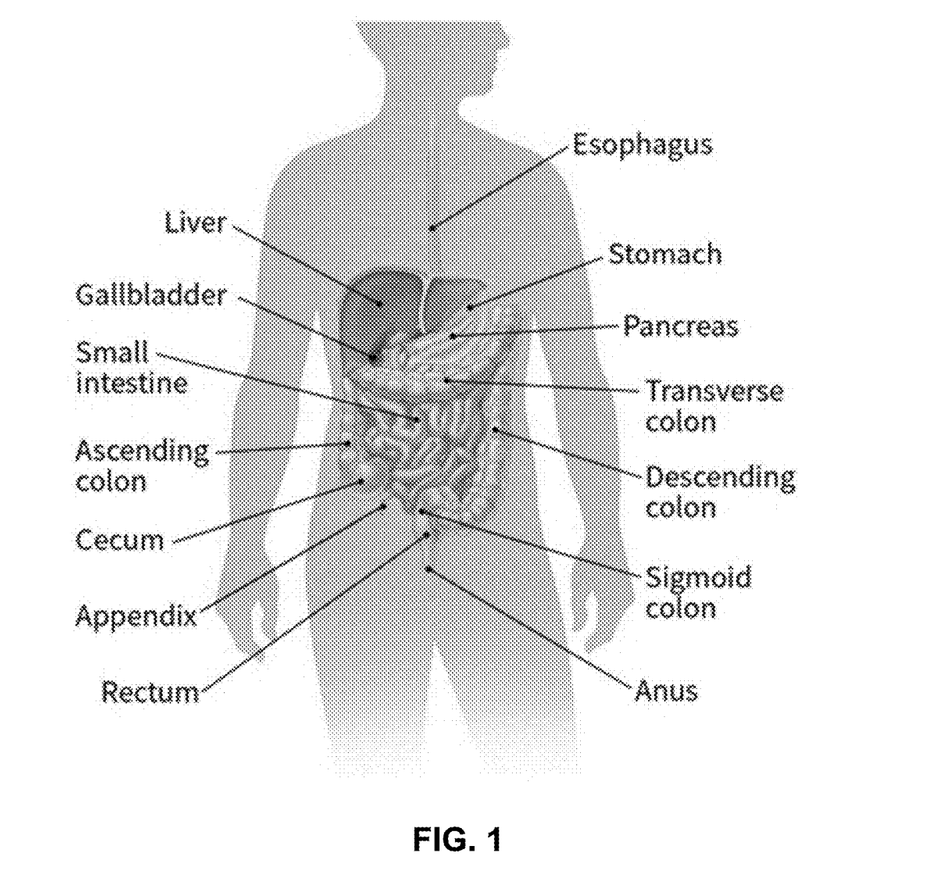
FIG. 1 depicts the colon and rectum as parts of the digestive system, which is also called the gastrointestinal (GI) system.

FIG. 1 depicts the colon and rectum as parts of the digestive system, which is also called the gastrointestinal (GI) system. The colon and rectum make up the large intestine (or large bowel). Most of the large intestine is made up of the colon, a muscular tube about 5 feet long. The parts of the colon are named by which way the food matter is traveling. The first section is called the ascending colon; it begins with a pouch called the cecum, where undigested food is received from the small intestine, and extends upward on the right side of the abdomen. The second section is called the transverse colon because it travels across the body from the right to the left side. The third section is called the descending colon because it descends (travels down) on the left side. The fourth section is called the sigmoid colon because of its "S" shape; the sigmoid colon joins the rectum, which connects to the anus. The ascending and transverse sections are collectively referred to as the proximal colon, and the descending and sigmoid colon are referred to as the distal colon.

Embodiments of the present invention include a fluorescence-based ingestible capsule and method of using the ingestible capsule for investigating the gastro-intestinal (GI) tract, in particular the colon. The embodiments overcome the problems and disadvantages of previously disclosed capsules for investigating the GI tract and fluorescence-based capsules for the GI tract.

In particular, the present invention resolves the problem of low sensitivity of the white light in detecting early and non-polypoid colorectal neoplasia, background noise in fluorescence-based systems, and dependence of measured intensity on many environmental parameters (source, detector, sensitivity peak, background, etc.).

Embodiments of the present invention resolve these problems and shortcomings of detection of non-polypoid colorectal neoplasia by detecting or measuring fluorescence lifetime of illuminated tissue and sensing the difference in fluorescence lifetime between cancerous and non-cancerous tissues.

In addition, the present invention does not suffer from bulky design, high cost and high-power consumption and is not limited to measuring only the intensity of endogenous fluorophore. Decay of the intensity is measured to determine fluorescence lifetime (FLT).

The device of the present invention has the advantages of relatively small dimension, low cost and low power consumption. The device offers the possibility of measuring the fluorescence lifetimes in addition to intensity which give it more flexibility.

Although the present invention is directed to early detection of colorectal disease, it is also applicable to explore the entire upper and lower parts of the gastro intestinal tract searching for abnormalities such as obscure gastrointestinal bleeding, Crohn's disease, small bowel tumors, polyposis syndromes, etc.

Capsule

Figure 2:
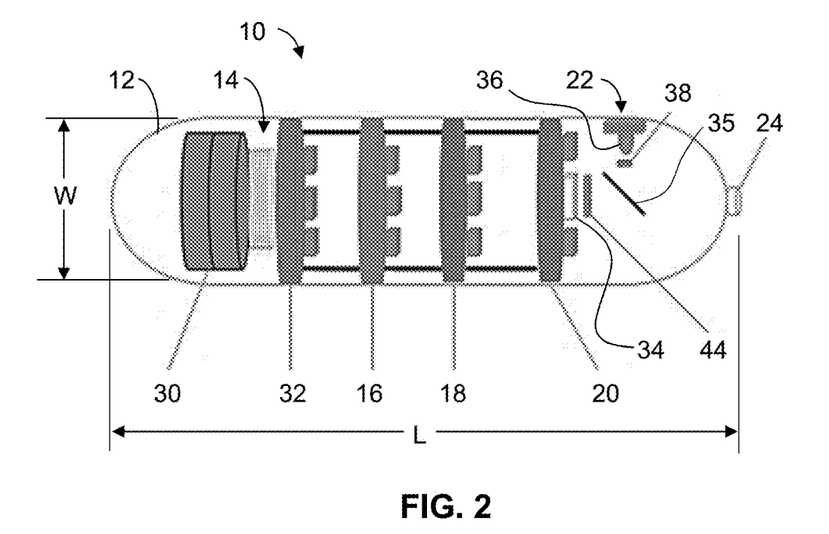
FIG. 2 is a schematic diagram showing an example capsule with one light source.
Figure 3:
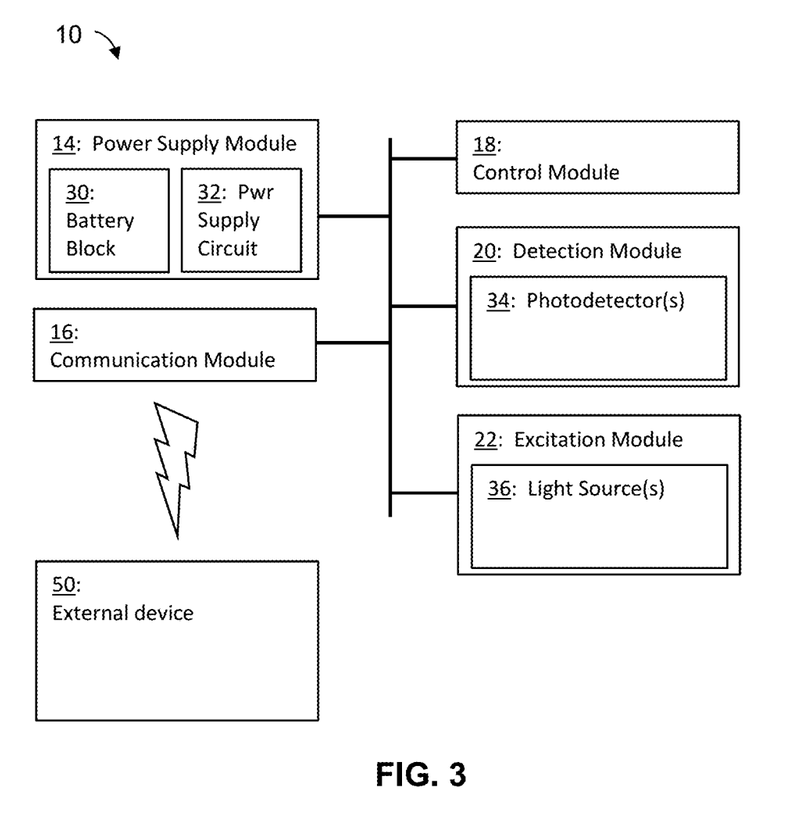
FIG. 3 is a block diagram of the capsule communicating with an external device.

Embodiments of the present invention include a capsule that can be ingested and swallowed by a patient. In FIGS. 2 and 3, capsule 10 has body 12 with a shape and size that allows the ingestion and swallowing by a patient. The shape and size further allow the capsule to pass through the esophagus into the stomach, into and through the small intestine, into and through the colon of the patient. The size of the capsule body is small enough to allow swallowing, but large enough to adequately contact the intestine during peristalsis. In one embodiment, the shape of capsule body 12 is a cylinder with hemispherical ends. Other shapes include, but are not limited to sphere or prolate spheroid. Capsule body 12 may be hollow to accommodate various system components. Capsule body 12 may be made of metal, plastic, glass, or ceramic material. Capsule body 12 may have a maximum length, L, of 3 cm and a maximum width (e.g., diameter), W, of 1.2 cm. These dimensions are small enough to allow swallowing, but large enough to adequately contact the intestine during peristalsis.

Capsule 10 comprises system components, namely power supply module 14, communication module 16, control module 18, detection module 20, and excitation module 22. The system components are contained within capsule body 12. Lens 24 is mounted on an aperture through capsule body 12.

Power Supply Module

Power supply module 14 includes two parts: battery block 30 and power supply circuit 32. For example, battery block 30 may include two SR44 series batteries (1.55 V, 195 mAh, 11.6 mm diameter×5.4 mm height). Preferably, battery block 30 stores sufficient power to allow capsule 10 to take measurements and transmit data for up to 9 hours. Power circuit 32 is configured to generate the voltage levels necessary to ensure the proper functioning of the electronic components that make up capsule 10. The voltage levels generated are independent of input voltage variation, load and noise. To do this, power circuit 32 includes small voltage regulators, which are fixed or adjustable, with one or more outputs and a minimum of external components. Suitable types of voltage regulators include, without limitation, linear, switching and charge pumps regulators.

Low drop out (LDO) linear regulators may be used if needed to have a voltage lower than the input voltage. In fact, LDO linear regulators have the specificity of having a low-voltage drop and resistance to noise at the output. To reverse the polarity or to generate higher-voltage levels, then charge pump regulators are to be used, unless the current is greater than their capacity, in which case the switching regulators may be used.

Communication Module

Communication module 16 acts as the communication interface between capsule 10 and the external environment. Communication module 16 includes electronic circuits and/or components. Communication module 16 is configured to send and receive data using radio signals. Design constraints for communication module 16 include size (for example, a maximum diameter of 1.8 cm), power consumption (as low as possible), operating frequency (for example, in the industrial, scientific and medical (ISM) radio bands), data rate of data send and receive. For example, communication module 16 is configured for wireless communication using Bluetooth technology. A Bluetooth transceiver module manufactured by STMicroelectronics (headquartered in Geneva, Switzerland) may be used in communication module 16.

Control Module

Control module 18 is configured to manage incoming and outgoing signals, data storage, and power. Control module 18 is configured to manage serial peripheral interface bus (SPI) communication with flash memory and universal asynchronous receiver-transmitter (UART) with the communication module 16, and other types of established communications depending on the integrated circuits. Control module 18 is the control base that decides what happens in capsule 10. Control module 18 functions as a communication interface between detection module 20 and communication module 16 processing the received signals. Control module 18 may include electronic circuits and/or components. Control module 18 may be in the form of a processor. Suitable processors include, without limitation, a Field-Programmable Gate Array (FPGA), a microcontroller, a Digital Signal Processor (DSP) and a Complex Programmable Logic Device (CPLD). CPLD does not need an external storage circuit as well as the other accompanying modules since it has a non-volatile architecture, making CPLD a preferred choice for use in control module 18.

Detection Module

Detection module 20 includes photodetector 34 configured to convert photons into detectable electronic (photoelectrons) signals by photoelectric effect (photoconductivity, photovoltaic and photo-emissive). Photons enter through lens 24 and pass through beam splitter 35 before reaching photodetector 34. Photodetector 34 is used to detect the intensity of the indocyanine green (ICG) fluorophore agent as well as the fluorescence lifetime (FLT) of the agent. ICG emits fluorescence between 750 nm and 950 nm, and at about 830 nm in blood. Fluorescence is in the near-infrared range, so photodetector 34 should be sensitive to near-infrared light. For example, photodetector 34 may be sensitive to light having wavelengths up to 1000 nm, more narrowly up to 900 nm, or more narrowly in the range of 350 nm to 900 nm. Since the light intensity emitted by ICG is low, a fast, sensitive photodetector with low noise and low-dark current is preferably used. For low-light detection applications, photodetectors with high internal multiplication of electrons (gain) and high Photon Detection Efficiency (PDE (%)) are preferred. Suitable types for photodetector 34 include, without limitation, vacuum photon detectors (PMTs), solid state photon detectors (e.g., EMCCD, ICCD, avalanche photodiodes (APD), Silicon Photomultiplier (SiPM), and visible light photon counters), and hybrid photon detectors (HPD).

A type of avalanche photodiode, namely a single-photon avalanche diode (SPAD), can have a gain that can reach more than $10^6$, which can eliminate a need for an additional amplifier. SPADs are preferred over standard photodiodes with no internal gain. Amplifiers would be needed if using standard photodiodes with no internal gain, and such amplifiers would increase readout noise and thus reduce the input dynamic range and the signal to noise ratio. Another advantage of an SPAD is its ability to detect the light emitted by a fluorophore at a concentration as low as 10 nM (nanomolar). SPADs are suitable since the concentration range used for the detection of colorectal cancer is in the range of some hundreds of nanomolars, and since SPADs are able to detect lifetime in the order of picoseconds. A commercially available SPAD-based detection system may be used to perform tests and extract characteristics in order to achieve a similar but miniaturized system. A limitation of SPADs is their small detection area, which limits signal harvesting since signal from spread isotropic light emitters cannot be efficiently focused into a small spot without significant losses. To address this limitation, photodetector 34 may be in the form of multiple SPADs, which are arranged in parallel, to increase the detection area of photodetector 34. Such an arrangement may form what is referred to as a silicon photomultiplier (SiPM). SiPM comprises a plurality of solid-state single-photon-sensitive devices based on single-photon avalanche diodes (SPADs) on a common silicon substrate. SiPM holds the advantages of both solid state and photocathode-based detectors. For example, photodetector 34 can be a commercial SiPM, such as a multi-pixel photon counter (MPPC) distributed by Hamamatsu Photonics K.K. (headquartered in Hamamatsu City, Japan). An MPPC is a photon-counting device using multiple avalanche photo-diode (APD) pixels operating in a Geiger mode.

Excitation Module

Excitation module 22 comprises light source 36 used to excite the fluorescent agent (indocyanine green (ICG)) with a light in the near-infrared range on the agent's maximum absorption peak of 780 nm. For example, near-infrared light from light source 36 may have wavelengths from 700 nm to 900 nm. Near-infrared light source 36 emits neither ultraviolet light (wavelengths less than 400 nm) nor visible light (wavelengths from 400 nm-700 nm) to avoid exciting endogenous fluorophores that are not of interest in measuring ICG emissions, and which, if excited, may lead to an incorrect detection result. Also, fluorescence emission from living tissue is weak and requires very sensitive light detectors and/or powerful illumination.

Near-infrared light from light source 36 is directed by beam splitter 35 to lens 24, where the near-infrared light is emitted out of capsule body 12. The emitted light illuminates tissues within the colon a patient. Excitation module 22 may comprise circuits and/or electronic components to support light source 36. Light source 36 may refer collectively to one or more sources of radiation. Suitable types for light source 36 include, without limitation, light-emitting diode (LED), laser diode (LD) and microLED.

A laser diode (LD) is a semiconductor device similar to a light-emitting diode in which a laser beam is created at the diode's junction. Suitable types of laser diodes include pulsed and continuous wave (CW) laser diodes. A continuous-wave laser diode produces a continuous, uninterrupted beam of light. A pulsed laser diode produced pulses of a beam of light having a specified pulse duration.

Excitation module 22 may comprise either one or both pulsed and CW laser diodes. The pulsed laser diode may produce pulses with a duration of 0.5 to 500 ns. The pulsed laser diode may produce ultrashort pulse durations in the range of 5 fs to 100 ps. The output power of the laser diodes may be in a range of few milliwatts to hundreds of milliwatts.

Figure 4:
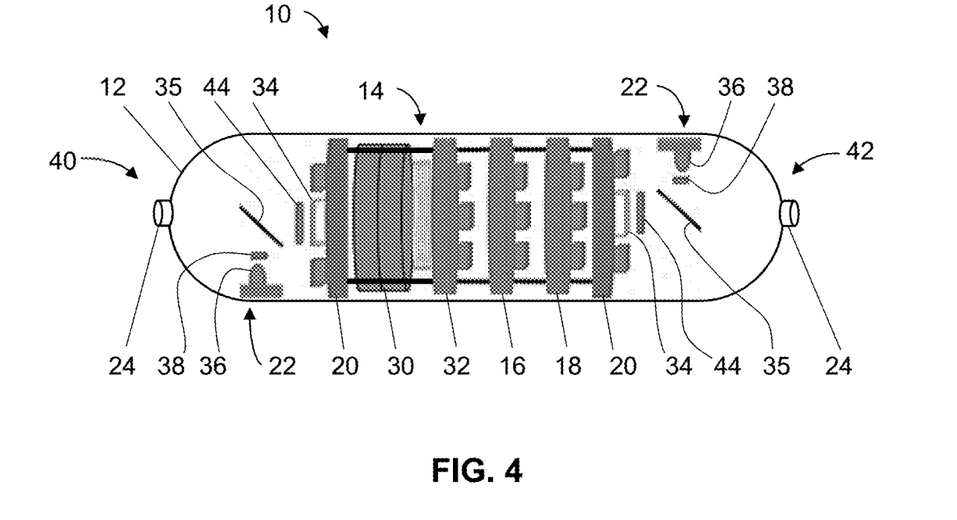
FIG. 4 is schematic diagram showing an example capsule with two light sources.

In FIG. 4, excitation module 22 is arranged at opposite ends of capsule body 12. Excitation module 22 comprises two light sources 36, one at each end of capsule body 12. One light source 36 comprises one or more pulse laser diodes capable of producing ultrashort pulse durations in the range of 5 fs to 100 ps. The other light source 36 comprises one or more CW laser diodes. The ultra-short pulse laser diode(s) is/are used for fluorescence lifetime (FLT) measurements. The continuous wave laser diode(s) is/are used for intensity measurements.

The tissues irradiated by light source 36 exhibit a fluorescence response. Light from light source 36 excites ICG fluorophore in the tissue which then emits light or fluoresce when the fluorophore returns to its ground state. Light source 36 may be used in combination with bandpass filter 38. ICG fluorescence from healthy tissues in the GI tract exhibits a spectrum around 830 nm when excited with a 780 nm light source.

Cancerous tissue exhibits a considerably lower fluorescence response than healthy tissue. The use of intensity to distinguish cancerous and noncancerous tissue is unreliable due to background noise in fluorescence-based systems and dependence of measured intensity on many environmental parameters.

The fluorescence lifetime of a fluorescence response of cancerous tissue is lower than healthy tissue and can be used to distinguish cancerous and healthy tissue. Fluorescence lifetime (FLT) measurements, unlike intensity measurements, are immune to environmental noise. Fluorescence lifetime is the time a fluorophore spends in the excited state before emitting a photon and returning to the ground state. FLT can vary from picoseconds to hundreds of nanoseconds depending on the fluorophore. The lifetime of a population of fluorophores is the time measured for the number of excited molecules to decay exponentially to N/e (36.8%) of the original population via the loss of energy through fluorescence or non-radiative processes.

Fluorescence lifetime (FLT) is an intrinsic property of a fluorophore. FLT does not depend on fluorophore concentration, absorption by the sample, sample thickness, method of measurement, fluorescence intensity, photobleaching, and/or excitation intensity. FLT is affected by external factors, such as temperature, polarity, and the presence of fluorescence quenchers. FLT is sensitive to internal factors that are dependent on fluorophore structure. Since FLT is immune to environmental factors, FLT measurements can be used to distinguish cancerous and noncancerous tissues without the disadvantages of fluorescence intensity.

Figure 5:
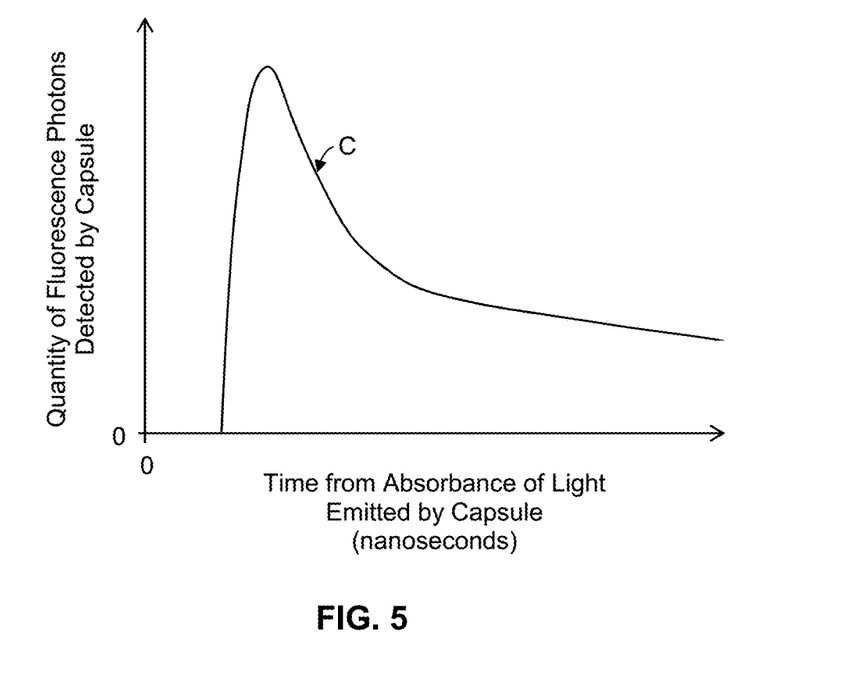
FIG. 5 is a graph showing example decay data representative of decay of intensity of a fluorescence response elicited by the capsule.

Fluorescence lifetime (FLT) can be measured in either the frequency domain or the time domain. The time domain method involves the illumination of a sample, such as tissue, with a short pulse of light, followed by measuring the emission intensity against time. The FLT is determined from the slope of the decay curve. Several fluorescence detection methods are available for lifetime measurements, of which, time-correlated single photon counting (TCSPC) enables simple data collection and enhanced quantitative photon counting. FIG. 5 shows example decay data obtained from the TCSPC method. Curve C represents decay of intensity of the fluorescence response caused by the short pulse of light from light source 36. FLT is calculated from the slope of the decay curve according to the following equation.

$$I(t)=I_o e^{-t/\tau}$$

In the above equation, t is the time after absorption of radiation, I(t) is intensity at time t, $I_o$ is intensity at time t=0, $\tau$ is FLT.

The frequency domain method involves the sinusoidal modulation of the incident light at high frequencies. In this method, the emission occurs at the same frequency as the incident light accompanied with a phase delay and change in the amplitude relative to the excitation light (demodulation).

Capsule 10 may employ a time domain method and/or a frequency domain method of measuring FLT. Although both methods may be used, the inventors have found that the time-domain method offers a significantly better separability of multiple lifetime targets than the frequency-domain approach.

Capsule 10 includes a system and components for fluorescence lifetime measurement. FLT measurement systems may be obtained, for example, from Hamamatsu Photonics K.K.

As previously mentioned, detection module 20 may include a multi-pixel photon counter (MPPC). In FIG. 4, detection module 20 is arranged at opposite ends of capsule body 12 and includes two MPPCs 34. One MPPC, at first end 40 of capsule body 12, is for fluorescence lifetime (FLT) measurements. The other MPPC, at second end 42 of capsule body 12, is for intensity measurements. Excitation module 22 is arranged at opposite ends of capsule body 12 and includes two different types of laser diodes 36: an ultra-short pulse laser diode and a continuous wave laser diode. The ultra-short pulse laser diode, at second end 42 of capsule body 12, is for FLT measurements. The continuous wave laser diode, at first end 40 of capsule body 12, is for fluorescence intensity measurements. In the case of continuous wave, the light is kept constant for a short period of time, typically few seconds, while the intensity is measured continuously. For FLT measurements, the light is pulsed using an ultra-short pulse laser diode, typically few picoseconds (e.g., 1 to 10 ps, or 1 to 20 ps), while the emitted fluorescence is measured during an observation window which is synchronized with the excitation pulses. Due to the random nature of the fluorescence emission, these measurements are repeated for several windows.

Once in the colon, capsule 10 powers on. Light source 36 emits an ultra short light pulse (e.g., near-infrared wavelengths including 780 nm) to excite colon tissue. Once excited, the ICG absorbs light and emits light to a longer wavelength. The optimal wavelength (830 nm) will be selected by filter 44. Filter 44 blocks out ICG excitation wavelength (780 nm) which if passed may lead to false detection results. Filter 44 does not block ICG fluorescence wavelengths (e.g., 830 nm). Photodetector 34 (e.g., an MPPC) detects photons from the ICG. Photodetector 34 data wirelessly via communication module 16 to device 50. The data (decay data) may include any of arrival times of detected photons, the quantity of detected photons, and change in quantity of detected photons over time. Device 50 is separate from capsule 10 and is located external to the patient. Examples for device 50 include, without limitation, a mobile phone, tablet, desktop computer, and laptop computer.

Figure 6:
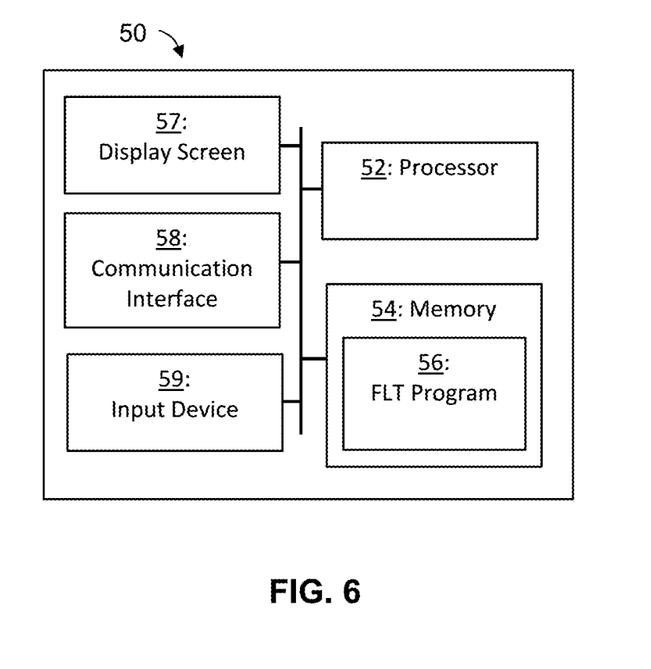
FIG. 6 is a block diagram of the external device.

In FIG. 6, device 50 comprises processor 52, memory 54 that stores FLT program 56, display screen 57, communication interface 58, and input device 59. Processor 52 comprises circuits and electronic components that execute instructions of an operating system and FLT program 56. FLT program 56 enables device 50 to perform various processes and functions described herein. Example elements for memory 54 include without limitation random-access memory (RAM) modules, read-only memory (ROM) modules, and other electronic data storage devices. Memory 54 may include a mass storage type of device such as a solid-state flash drive, CD drive, and DVD drive. Memory 54 comprises a non-transitory computer readable medium that stores FLT program 56 that contain instructions for performing various processes and functions described herein. Examples for display screen 57 include, without limitation, LCD, LED, and OLED screens. Communication interface 58 comprises circuits and electronic components configured to send and receive data to/from capsule 10. Data communication is wireless, such as by using Bluetooth technology. Examples for input device 59 include, without limitation, a keyboard, a microphone, and a touch sensitive layer over display screen 57.

Figure 7:
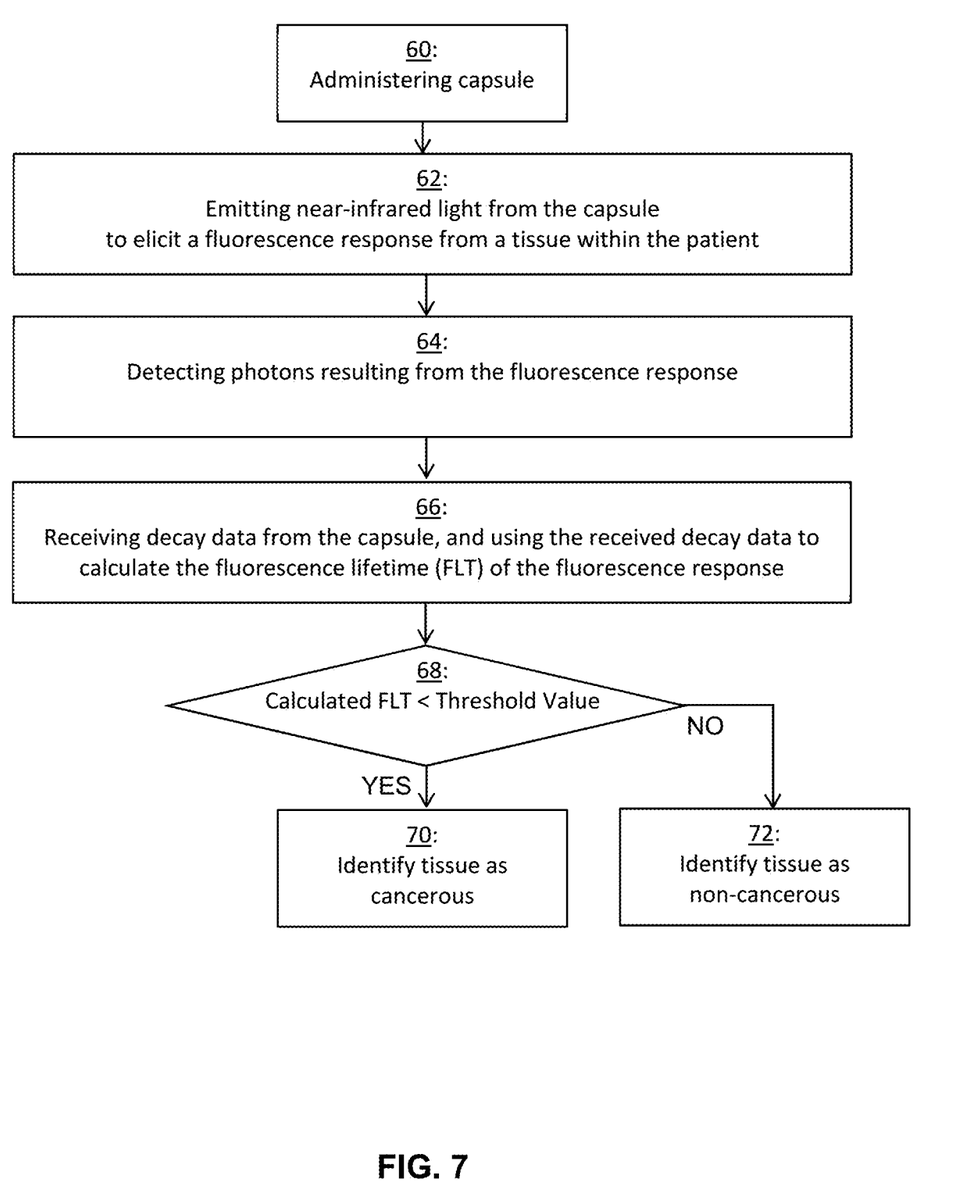
FIG. 7 is a flow diagram showing an example method for investigating issue of a patient.

In FIG. 7, an example method includes administering capsule 10 to a patient at block 60. Next at block 62, when capsule 10 is in the patient, near-infrared light is emitted from at least one light source 36 to elicit a fluorescence response from a tissue within the patient. At block 64, at least one photodetector 34 detects photons resulting from the fluorescence response (fluorescence photons).

At block 66, data is communicated by communication module 16 of capsule 10 to communication interface 58 of device 50. The data (decay data) may include any of arrival times of detected fluorescence photons, the quantity of detected photons, and change in quantity of detected photons over time. Due to decay, the quantity of fluorescence photons decreases over the period of time. Such data received by device 50 is referred to as decay data. By running program 56, processor 52 uses the received decay data to calculate fluorescence lifetime (FLT) as previously described.

Device 50 may distinguish cancerous tissue from healthy tissue based on the calculated FLT. As mentioned above, the FLT of a fluorescence response of cancerous tissue is lower than healthy tissue. At block 68, processor 52 determines whether the calculated FLT is below a threshold value. The threshold value may be based on FLT of healthy tissue. For example, the threshold value may be equal to FLT of healthy tissue or a marginal percentage (e.g., 5%) below FLT of healthy tissue. FLT of healthy tissue may be known in advance, prior to administration of capsule 10 to the patient. FLT of healthy tissue or the threshold value may be entered by a user via input device 59. Alternatively, FLT of healthy tissue may be determined by processor 52 from data transmitted from capsule 10 after administration of capsule 10 to the patient.

Device 50 identifies tissue as either cancerous or non-cancerous based on the calculated fluorescence lifetime. If YES at block 68 (calculated FLT is below the threshold value), then device 50 identifies tissue as cancerous at block 70. If NO at block 68 (calculated FLT greater than or equal to the threshold value), then device 50 identifies tissue as non-cancerous at block 72. The result at block 70 or 72 may be shown by device 50 on its display screen 57.

Probe

Further embodiments of the present invention include a fluorescence-based probe for investigating the gastro-intestinal (GI) tract, in particular the colon. The probe is a wire-based grouping of modules (e.g., 20 and 22, and optionally 14, 16, and 18). The probe may be used to demonstrate a method for early detection of colorectal cancerous tissue.

EXAMPLE

A prototype capsule was assembled using commercially available components. The prototype capsule included an ultra short pulsed laser diode and a continuous wave laser diode for intensity measurements and fluorescence lifetime measurements, respectively. The prototype capsule included MPPCs. To test the MPPCs, an evaluation board from Hamamatsu Photonics K.K. was used. The evaluation board contains the circuitry needed for the power supply and control modules to operate the MPPC.

Introducing such a capsule as an alternative solution to the existing white light capsule will make it possible to detect non-polypoid colon lesions based on advantages of fluorescence sensing.

While several particular forms of the invention have been illustrated and described, it will also be apparent that various modifications may be made without departing from the scope of the invention. It is also contemplated that various combinations or subcombinations of the specific features and aspects of the disclosed embodiments may be combined with or substituted for one another in order to form varying modes of the invention. Accordingly, it is not intended that the invention be limited, except as by the appended claims.

What is claimed is:

1. An ingestible capsule for detecting cancerous and non-cancerous tissues, comprising:
    a capsule body;
    an excitation module in the capsule body, the excitation module comprising at least one light source configured to generate near-infrared light that elicits a fluorescence response from tissue of a patient;
    a detection module in the capsule body, the detection module comprising at least one photodetector configured to detect photons resulting from the fluorescence response, and detect a fluorescence lifetime of a fluorescent agent used to treat the tissue of the patient;
    a communication module in the capsule body, the communication module including electronic components configured to transmit decay data using radio signals while the capsule is in the patient, the decay data representative of decay of intensity of the fluorescence response;
    a device configured to receive the decay data from the capsule while the capsule is in the patient and while the device is external to the patient, and configured to use the received decay data to calculate a fluorescence lifetime of the fluorescence response;
    a processor configured to determine whether the calculated fluorescence lifetime is below a threshold value based on a fluorescence lifetime of healthy tissue;
    a first lens and a second lens, wherein the first lens is mounted on a first aperture through the capsule body at a first end of the capsule body, and wherein the second lens is mounted on a second aperture through the capsule body at a second end of the capsule body opposite the first end; and
    a first beam splitter and a second beam splitter, wherein the first beam splitter is disposed at the first end of the capsule body, wherein the second beam splitter is disposed at the second end of the capsule body opposite the first end, and wherein the first beam splitter and the second beam splitter are configured to respectively direct the near-infrared light to the first lens and the second lens,
    wherein the fluorescence lifetime of the fluorescent agent represents a time a fluorophore is in an excited state before emitting a photon and returning to a ground state,
    wherein the at least one light source comprises a continuous wave laser diode at the first end of the capsule body and a pulsed laser diode at the second end of the capsule body opposite the first end, and
    wherein the at least one photodetector comprises a first photodetector at the first end of the capsule body adjacent to the first continuous wave laser diode, and a second photodetector at the second end of the capsule body opposite the first end and adjacent to the pulsed laser diode.

2. The ingestible capsule of claim 1, wherein the at least one photodetector comprises a silicon photomultiplier comprising a plurality of solid-state single-photon-sensitive devices.

3. The ingestible capsule of claim 1, wherein the at least one photodetector comprises a first silicon photomultiplier at a first end of the capsule body and second silicon photomultiplier at a second end of the capsule body.

4. The ingestible capsule of claim 1, wherein the at least one light source is configured to generate near-infrared light that elicits a fluorescence response from tissue of the patient treated with indocyanine green as the fluorescent agent.

5. The system of claim 1, wherein the device is selected from the group consisting of a mobile phone, tablet, desktop computer, and laptop computer.

6. The system of claim 1, wherein the device is configured to identify the tissue as either cancerous or non-cancerous based on the calculated fluorescence lifetime.

7. A method of investigating a tissue of a patient, comprising:
    administering a capsule to a patient;
    when the capsule is in the patient, emitting near-infrared light from at least one light source in the capsule to elicit a fluorescence response from a tissue within the patient treated with indocyanine green as a fluorescent agent;
    detecting, by at least one photodetector in the capsule, photons resulting from the fluorescence response;
    communicating decay data from the capsule while the capsule is in the patient, the decay data representative of decay of intensity of the fluorescence response;
    receiving the decay data from the capsule while the capsule is in the patient, and using the received decay data to calculate a fluorescence lifetime of the fluorescence response;
    determining whether the calculated fluorescence lifetime is below a threshold value based on a fluorescence lifetime of healthy tissue; and
    directing, by a first beam splitter and a second beam splitter, the near-infrared light to a first lens and a second lens, respectively,
    wherein the fluorescence lifetime of the fluorescence response represents a time a fluorophore is in an excited state before emitting a photon and returning to a ground state, wherein the at least one light source comprises a continuous wave laser diode at a first end of a capsule body and a pulsed laser diode at a second end of the capsule body opposite the first end, wherein the at least one photodetector comprises a first photodetector at the first end of the capsule body adjacent to the first continuous wave laser diode, and a second photodetector at the second end of the capsule body opposite the first end and adjacent to the pulsed laser diode, wherein the first lens is mounted on a first aperture through the capsule body at the first end of the capsule body, wherein the second lens is mounted on a second aperture through the capsule body at a second end of the capsule body opposite the first end, wherein the first beam splitter is disposed at the first end of the capsule body, and wherein the second beam splitter is disposed at the second end of the capsule body opposite the first end.

8. The method of claim 7, further comprising identifying the tissue as either cancerous or non-cancerous based on the calculated fluorescence lifetime.

\* \* \* \* \*